US010071061B2

(12) United States Patent
Kageyama et al.

(10) Patent No.: US 10,071,061 B2
(45) Date of Patent: Sep. 11, 2018

(54) STERILE COMPOSITION

(71) Applicants: TEIJIN LIMITED, Osaka-shi, Osaka (JP); Teijin Pharma Limited, Tokyo (JP); THE CHEMO-SERO-THERAPEUTIC RESEARCH INSTITUTE, Kumamoto-shi, Kumamoto (JP)

(72) Inventors: Yukako Kageyama, Tokyo (JP); Kentaro Fujinaga, Tokyo (JP); Ayuko Yamaguchi, Tokyo (JP); Susumu Honda, Tokyo (JP); Makoto Satake, Tokyo (JP); Hiroaki Kaneko, Tokyo (JP); Ayumi Ishiwari, Tokyo (JP)

(73) Assignees: TEIJIN LIMITED, Osaka (JP); Teijin Pharma Limited, Chiyoda-ku, Tokyo (JP); THE CHEMO-SERO-THERAPEUTIC RESEARCH INSTITUTE, Kyokushi Kikuchi, Kumamoto (JP)

( * ) Notice: Subject to any disclaimer, the term of this patent is extended or adjusted under 35 U.S.C. 154(b) by 0 days.

(21) Appl. No.: 14/400,732

(22) PCT Filed: May 13, 2013

(86) PCT No.: PCT/JP2013/063868
§ 371 (c)(1),
(2) Date: Nov. 12, 2014

(87) PCT Pub. No.: WO2013/172468
PCT Pub. Date: Nov. 21, 2013

(65) Prior Publication Data
US 2015/0125511 A1    May 7, 2015

(30) Foreign Application Priority Data

May 14, 2012   (JP) .................. 2012-110390
May 14, 2012   (JP) .................. 2012-110765
Mar. 1, 2013   (JP) .................. 2013-040593

(51) Int. Cl.
| A61K 9/70 | (2006.01) |
| A61K 38/36 | (2006.01) |
| A61K 38/46 | (2006.01) |
| A61K 38/48 | (2006.01) |
| A61K 9/00 | (2006.01) |
| A61K 38/47 | (2006.01) |
| A61K 47/34 | (2017.01) |

(52) U.S. Cl.
CPC ........... *A61K 9/70* (2013.01); *A61K 9/0024* (2013.01); *A61K 38/363* (2013.01); *A61K 38/465* (2013.01); *A61K 38/47* (2013.01); *A61K 38/4833* (2013.01); *C12Y 302/01021* (2013.01); *C12Y 304/21005* (2013.01); *A61K 47/34* (2013.01); *C12Y 301/01003* (2013.01)

(58) Field of Classification Search
None
See application file for complete search history.

(56) References Cited

U.S. PATENT DOCUMENTS

| 5,134,122 A | 7/1992 | Orsolini |
| 5,192,741 A | 3/1993 | Orsolini et al. |
| 5,225,205 A | 7/1993 | Orsolini |
| 5,439,688 A | 8/1995 | Orsolini et al. |
| 5,445,832 A | 8/1995 | Orsolini et al. |
| 5,597,897 A | 1/1997 | Ron et al. |
| 5,637,568 A | 6/1997 | Orsolini et al. |
| 5,730,933 A | 3/1998 | Peterson |
| 5,776,885 A | 7/1998 | Orsolini et al. |
| 5,945,128 A | 8/1999 | Deghenghi |
| 2009/0305957 A1 | 12/2009 | Moore et al. |
| 2010/0151033 A1 | 6/2010 | Ahlheim et al. |
| 2011/0280919 A1 | 11/2011 | Moloye-Olabisi et al. |
| 2012/0121532 A1* | 5/2012 | Goessl ............... A61K 9/0014 424/78.35 |

FOREIGN PATENT DOCUMENTS

| EP | 0437095 | 8/1999 |
| EP | 0562864 | 12/2005 |
| JP | 01-121222 A | 5/1989 |
| JP | 2203861 A | 8/1990 |
| JP | 03-66625 A | 3/1991 |
| JP | 05-221855 A | 8/1993 |
| JP | 06-172208 A | 6/1994 |
| JP | 06-508777 A | 10/1994 |
| JP | 11-514678 A | 12/1999 |
| JP | 2010-506965 A | 3/2010 |
| JP | 2011-47089 A | 3/2011 |
| JP | 201147089 | 3/2011 |
| WO | 9300050 | 1/1993 |
| WO | 9809613 | 3/1998 |
| WO | 00/33893 A1 | 6/2000 |
| WO | 2000033893 | 6/2000 |
| WO | 2008045516 | 4/2008 |
| WO | 2010/079047 A2 | 7/2010 |
| WO | 2011/146359 A1 | 11/2011 |

OTHER PUBLICATIONS

Gaomboa-Martinez et al., "Fibrin coating on poly (L-lactide) scaffolds for tissue engineering", Journal of Bioactive and Compatible Polymers, 0(0): 1-14.*
Ho et al., "The Evaluation of a Biphasic Osteochondral Implant Coupled with an Electrospun Membrane in a Large Animal Model", Tissue Engineering: Part A, 2010, vol. 16, No. 4, pp. 1123-1141. DOI: 10.1089=ten.tea.2009.0471.*
Guarino et al., "hMSC interaction with PCL and PCL/gelatin platforms: A comparative study on films and electrospun membranes", Journal of Bioactive and Compatible Polymers, 2011, 26(2), pp. 144-160. DOI: 10.1177/0883911511399410.*

(Continued)

*Primary Examiner* — Suzanne Marie Noakes
(74) *Attorney, Agent, or Firm* — Sughrue Mion, PLLC (57) ABSTRACT

A sterile composition which comprises a protein and an aliphatic polyester containing the protein and is sterilized with radiation. In this sterile composition, the structure and function (activity) of the protein are retained.

6 Claims, 1 Drawing Sheet

(56) References Cited

OTHER PUBLICATIONS

Li et al., "Preparation and biodegradation of electrospun PLLA/keratin nonwoven fibrous membrane", Polymer Degradation and Stability, 2009, vol. 94, pp. 1800-1807.*
Communication dated Jan. 21, 2015, issued by the Japanese Patent Office in counterpart Application No. 2014515698.
Communication dated Mar. 18, 2015 from the European Patent Office in counterpart application No. 13791568.2.
Jain S et al: "A two-stage strategy for sterilization of poly(lactide-co-glycolide) particles by gamma-irradiation does not impair their potency for vaccine delivery", J Pharm Sci, vol. 100, No. 2, Feb. 2011 (Feb. 2011), pp. 646-654.
International Search Report for PCT/JP2013/063868, dated Jul. 16, 2013.
International Preliminary Report for PCT/JP2013/063868 dated Nov. 18, 2014, along with the Written Opinion.

* cited by examiner

STERILE COMPOSITION

CROSS REFERENCE TO RELATED APPLICATIONS

This application is a National Stage of International Application No. PCT/JP2013/063868, filed May 13, 2013, claiming priority based on Japanese Patent Application Nos. 2012-110390 filed May 14, 2012, JP 2012-110765, filed May 14, 2012 and JP 2013-040593 filed Mar. 1, 2013, the contents of all of which are incorporated herein by reference in their entirety.

TECHNICAL FIELD

The present invention relates to a sterile composition of a protein which retains its function as it is contained in an aliphatic polyester.

BACKGROUND ART

Natural and synthetic proteins are becoming more and more important as drugs. When they are used for medical applications, their products must be sterilized. As means of sterilization, there are known heat sterilization in an autoclave, sterilization with ionizing radiation such as a γ ray or electron beam, gas sterilization with an ethylene oxide gas, plasma sterilization with hydrogen peroxide, and separate sterilization using a chemical sterilant comprising a glutaraldehyde formulation or a filter. However, the activities of proteins such as bioactive proteins are reduced by sterilization with heat or radiation. Sterilization with ethylene oxide has possibilities that a by-product may be produced by a chemical reaction and that a highly toxic residual gas may adversely affect the human body. Sterilization with a chemical sterilant has a problem that the resistance to a sterilant of a protein and changes in pH, ion intensity and temperature must be taken into consideration. Then, to manufacture pharmaceuticals and medical products containing or immobilizing a protein, their production processes must be entirely made in sterile conditions and a huge amount of production cost is required.

Although a solution containing a protein is subjected to separate sterilization with a filter, it is difficult to apply this separate sterilization to a composition containing large particles or a solid or semisolid composition.

EP0437095 teaches that a neutralized oxidized cellulose product combined with heparin or a heparin fragment (nORC) can be sterilized by gamma-ray irradiation. However, this document fails to teach the sterilization of ORC or n-ORC to which a protein is bound.

EP0562864 discloses a composite wound care substance containing a collagen sponge matrix, a second bioabsorbable polymer such as an oxidized regenerated cellulose (ORC) dispersed fiber and an active agent such as peptide. This document teaches that the active agent may be contained in the matrix, the bioabsorbable polymer or both of them and that the composite sponge substance can be sterilized while it is packaged.

U.S. Pat. No. 5,730,933 discloses a method of sterilizing biologically active peptide with gamma-ray or electron-beam irradiation without the loss of the biological activity of the peptide. This method is a technology comprising the steps of forming a mixture of biologically active peptide and a foreign protein such as gelatin, freezing or lyophilizing this mixture, and irradiating it. This document teaches that the existence of the foreign protein stabilizes peptide and prevents the reduction of the activity of peptide.

WO2000/033893 discloses a complex of therapeutic peptide and a polysaccharide selected from the group consisting of oxidized regenerated cellulose, neutralized oxidized regenerated cellulose and mixtures thereof. This document teaches that when peptide is formulated together with an effective amount of the polysaccharide before sterilization with ionizing radiation, the biological activity of the peptide therapeutic agent is not lost and is stabilized if peptide is sterilized with ionizing radiation.

However, these documents do not suggest that the structural change such as aggregation and deactivation of a protein which occur during sterilization with ionizing radiation can be suppressed by an aliphatic polyester.

Meanwhile, JP-A 2011-47089 discloses a process for producing an enzyme-containing nanofiber having excellent enzyme activity. In this process, a spinning solution containing an enzyme and a polymer dissolved in a nonaqueous solvent is spun by an electrostatic spinning method to form a zymogen nanofiber which is then imparted with water and dried. However, this document is silent about the sterilization of the enzyme-containing nanofiber.

DISCLOSURE OF THE INVENTION

It is an object of the present invention to provide a sterile composition which retains the structure and function of a protein.

The inventors of the present invention conducted intensive studies to solve the above problem and found that, surprisingly, when a protein is contained in an aliphatic polyester, the structural change and functional deterioration of the protein caused by sterilization with radiation and either one or both of the above change and the above deterioration caused by storage after sterilization with radiation can be suppressed. The present invention was accomplished based on this finding.

That is, the present invention is a sterile composition which comprises a protein and an aliphatic polyester containing the protein and is sterilized with radiation.

BEST MODE FOR CARRYING OUT THE INVENTION

The present invention is a sterile composition which comprises a protein and an aliphatic polyester containing the protein and is sterilized with radiation.

The protein used in the present invention is not particularly limited. Preferred examples of the protein include hemostat proteins typified by fibrinogen and thrombin, enzymes typified by asparaginase, catalase, superoxide dismutase and lipase, transport proteins typified by hemoglobin, serum albumin and low density lipoprotein, muscle proteins typified by actin and myosin, defense proteins typified by antibodies and complements, toxin proteins typified by diphtheria toxin, botulinum toxin and snake venom, protein hormones typified by insulin, growth factors and cytokine, storage proteins typified by ovalbumin and ferritin, structural proteins typified by collagen and keratin, and growth factors typified by epidermal growth factor (EGF), insulin-like growth factor (IGF), transforming growth factor (TGF), nerve growth factor (NGF), brain-derived neurotrophic factor (BDNF), vascular endothelial growth factor (VEGF), granulocyte-colony stimulating factor (G-CSF), granulocyte-macrophage-colony stimulating factor (GM-CSF), platelet-derived growth factor (PDGF), erythropoietin (EPO), thrombopoietin (TPO), basic fibroblast growth factor (bFGF or FGF2) and hepatocyte growth factor (HGF). Out of these, enzymes, transport proteins, muscle proteins, defense proteins, toxin proteins, protein hormones, storage proteins, structural proteins and growth factors are particularly preferred.

The protein used in the present invention may be of animal origin or manufactured by a genetic recombination technique. If it is of animal origin, it is preferably of human origin. The protein manufactured by the genetic recombination technique may be a variant obtained by replacing the amino acid sequence to another amino acid sequence if the essential bioactivity is the same. Proteins obtained by modifying these proteins and mixtures thereof may also be used.

To the protein used in the present invention, additives which are pharmaceutically acceptable may be added.

Preferred examples of the additives include blood coagulation factor XIII, albumin, isoleucine, glycine, arginine, glutamic acid, phenylalanine, histidine, surfactants, sodium chloride, sugar alcohols (such as glycerol, mannitol, etc.), trehalose, sodium citrate, aprotinin and calcium chloride. At least one selected from the group of these is used.

The protein used in the present invention or a mixture of the protein and additives may be dispersed in an aliphatic polyester as molecules but preferably as particles formed by the aggregation of the molecules (may be referred to as "protein particles" including mixed particles with the additives).

The aliphatic polyester used in the present invention is preferably a bioabsorbable or biodegradable polymer. Examples of the bioabsorbable polymer include polylactic acid, polyglycolic acid, polylactic acid-polyglycolic acid copolymer, polycaprolactone, polylactic acid-polycaprolactone copolymer, polyglycerol sebacic acid, polyhydroxy alkanoic acid, polybutylene succinate and derivatives thereof.

Out of these, polyglycolic acid, polylactic acid, polycaprolactone, copolymers thereof and mixtures thereof are preferred, and polylactic acid and polylactic acid-glycolic acid copolymer are most preferred. For example, a stereocomplex of poly-L-lactic acid and poly-D-lactic acid may be used.

The molecular weight of the aliphatic polyester used in the present invention is $1 \times 10^3$ to $5 \times 10^6$, preferably $1 \times 10^4$ to $1 \times 10^6$, much more preferably $5 \times 10^4$ to $5 \times 10^5$. The terminal structure of the polymer and a catalyst for polymerizing the polymer may be arbitrarily selected.

In the sterile composition of the present invention, another polymer or another compound may be used in combination as long as the object of the present invention is not impaired. Examples of these include copolymers, polymer blends and compound mixtures.

The aliphatic polyester used in the present invention preferably has high purity. Especially, the contents of additives and plasticizer contained in the aliphatic polyester and residues such as residual catalyst, residual monomers and residual solvent used for molding and post-processing are preferably as low as possible. Especially when the composition is used for medical purposes, it is necessary to reduce these contents to values below safety standards.

In the present invention, the expression "containing the protein" means that at least part of the protein enters the inside of the aliphatic polyester. This state is distinguished from the state of a lyophilized complex in which the protein is existent on the surface of the composition or in the voids of the composition.

The form of the sterile composition of the present invention is not particularly limited, and the composition may be in the form of a fiber, film, sheet, plate-like body, tube-like body, linear body, rod-like body, cushion material, foam or porous body. The molding method for producing a molded product is not particularly limited if it is a method in which the structural change and the reduction of the activity of the protein are suppressed. For example, suitable molding techniques such as extrusion molding, injection molding, calendar molding, compression molding, blow molding, vacuum forming, powder molding, cast molding and casting may be employed. The sterile composition of the present invention is suitable for the production of fibers and films, and any one of molding techniques which have been employed for the production of plastic fibers or films may be employed. For example, extrusion molding techniques such as inflation extrusion molding and T die extrusion molding, and calendering and casting techniques may be used. The above molding may be melt molding or solution molding, out of which solution molding is preferred in order to facilitate the dispersion of the protein so as to prevent the functional deterioration of the protein.

The fiber form as used herein refers to a 3-D molded body formed by the lamination, weaving, knitting or another technique of one or a plurality of fibers. The fiber form is, for example, a nonwoven fabric. Further, a tube and a mesh obtained by processing the nonwoven fabric are included in the fiber form.

The average fiber diameter of the sterile composition having a fiber form of the present invention is, for example, 0.01 to 50 μm and may be suitably determined by a person skilled in the art according to the intended use.

The sterile composition having a fiber form of the present invention may be in the form of a long fiber. The long fiber is a fiber formed without adding the step of cutting a fiber in the course of transition from spinning to the processing of a fiber molded body. It can be formed by electrospinning, span bonding and melt blowing methods. Out of these, the electrospinning method is preferred.

The electrospinning method is a method in which a fiber molded body is obtained on an electrode by applying a high voltage to a solution containing a polymer. The process comprises the steps of preparing a spinning solution containing a polymer, applying a high voltage to the solution, jetting the solution, forming a fiber molded body by evaporating the solvent, from the jetted solution, eliminating the charge of the formed fiber molded body as an optional step, and accumulating the fiber molded body by the charge loss.

A description is subsequently given of the process for producing a sterile composition having a fiber form or a nonwoven fabric form out of the invention, taking the electrospinning method as an example.

The step of preparing a spinning solution in the electrospinning method will be explained. Although the spinning solution in the present invention is not particularly limited, an emulsion containing an organic solvent solution of an aliphatic polyester and an aqueous solution of a protein, a suspension containing an organic solvent solution of an aliphatic polyester and protein particles, or an organic solvent solution containing an aliphatic polyester and a protein may be used as the spinning solution. Out of these, a suspension containing an organic solvent solution of an aliphatic polyester and protein particles is preferred.

The concentration of the aliphatic polyester in the aliphatic polyester solution is preferably 1 to 30 wt %. When the concentration of the aliphatic polyester is lower than 1 wt %, it is difficult to form a fiber molded body disadvantageously. When the concentration is higher than 30 wt %, the fiber diameter of the obtained fiber molded body becomes large disadvantageously. The concentration of the aliphatic polyester contained in the organic solvent solution is more preferably 2 to 20 wt %.

The solvent for the aliphatic polyester is not particularly limited if it can dissolve the aliphatic polyester, evaporates in the spinning step and can form a fiber. Only one solvent or a combination of two or more solvents may be used. Examples of the solvent include chloroform, 2-propanol, toluene, benzene, benzyl alcohol, dichloromethane, carbon tetrachloride, cyclohexane, cyclohexanone, trichloroethane, methyl ethyl ketone, ethyl acetate and mixtures thereof. To form an emulsion, a solvent such as acetone, ethanol, methanol, tetrahydrofuran, 1,4-dioxane, 1-propanol, phenol, pyridine, acetic acid, formic acid, hexafluoro-2-propanol, hexafluoroacetone, N,N-dimethylformamide, N,N-dimethylacetamide, acetonitrile, N-methyl-2-pyrrolidinone, N-methylmorpholine-N-oxide or 1,3-dioxolane may be contained. Out of these, dichloromethane or ethanol is preferably used from the viewpoints of handling ease and physical properties.

The protein in the present invention may be added to and mixed with an organic solvent solution of an aliphatic polyester in a solid, liquid or solution form.

In the present invention, when the emulsion containing an organic solvent solution of an aliphatic polyester and an aqueous solution of a protein is used as the spinning solution, the aqueous solvent for the protein is not particularly limited if it can dissolve the protein, forms an emulsion with the organic solvent solution of an aliphatic polyester, evaporates in the spinning step and can form a fiber. For example, physiological saline and buffer solutions may be used. Further, a stabilizer for the protein and additives may be added. Out of these, a phosphoric acid buffer solution or physiological saline is preferably used.

The concentration of the protein in the aqueous solution of the protein used in the present invention is not particularly limited and may be suitably determined according to the characteristic properties of the protein. It is, for example, 0.5 to 50 wt %.

To prepare an emulsion from an organic solvent solution of an aliphatic polyester and an aqueous solution of a protein, the mixing ratio of these solutions is not particularly limited if they form a stable emulsion. For example, the (aqueous solution of protein)/(organic solvent solution of aliphatic polyester) (volume ratio) is 1/100 to 1/2. When this value is larger than 1/2, the emulsion becomes unstable disadvantageously.

Although the method of preparing an emulsion by mixing together an organic solvent solution of an aliphatic polyester and an aqueous solution of a protein is not particularly limited, ultraviolet waves or stirring means may be used. As the stirring means, high-speed stirring means such as a homogenizer or stirring means such as an attriter or ball mill may be used. Out of these, dispersion with ultrasonic waves is preferred.

Also, the spinning solution may be prepared by adding an aliphatic polyester after an emulsion is formed from an organic solvent and an aqueous solution of a protein.

In the present invention, when a suspension containing an organic solvent solution of an aliphatic polyester and a protein is used as the spinning solution, the sizes of protein particles are not particularly limited but preferably 0.01 to 100 μm. It is technically difficult to manufacture protein particles having a particle size smaller than 0.01 μm, and when the particle size is larger than 100 μm, dispersibility degrades and the sterile composition becomes brittle disadvantageously.

Although the method of preparing a suspension by mixing together an organic solvent solution of an aliphatic polyester and protein particles is not particularly limited, ultraviolet waves or stirring means may be used. As the stirring means, high-speed stirring means such as a homogenizer or stirring means such as an attriter or ball mill may be used. Out of these, dispersion with ultrasonic waves is preferred.

Further, the spinning solution may be prepared by adding an aliphatic polyester after a suspension is formed from an organic solvent and protein particles.

Before the preparation of the suspension, protein particles may be microfabricated. For microfabrication, there are dry milling and wet milling both of which may be employed and also may be combined in the present invention.

Dry milling may be carried out by milling with a ball mill, planetary mill or oscillating mill, by pounding in a mortar with a pestle, or by grinding with a medium stirring type pulverizer, jet mill or stone mill.

Meanwhile, wet milling is carried out by stirring with a stirrer or kneader having high shear force while protein particles are dispersed in a suitable dispersion medium, or by using a ball mill or bead mill while protein particles are dispersed in a medium. Further, protein particles produced by a spay drier may also be used.

The sterilization method used in the present invention is radiation sterilization. Examples of the radiation in use include alpha rays, beta rays, gamma rays, neutron rays, electron beams and X-rays. Out of these, gamma rays and electron beams are preferred, and electron beams are most preferred. Although the sterilization method is not particularly limited, the dose of the radiation is 10 to 80 kGy, preferably 20 to 30 kGy. Although the temperature condition is not particularly limited, it is −80 to 40° C., preferably −80 to 30° C.

The radiation such as alpha rays, positron, gamma rays, neutron rays, electron beams or X-rays strips an electron off from molecules or atoms constituting a substance when it is applied to the substance. A molecular bond is broken upon this, and a highly reactive radical is produced and chemically reacts with a surrounding substance secondarily.

It is well known that a protein tends to lose its function (activity) upon exposure to radiation. This is considered to be due to the destruction of "a high-order structure" which is a source of developing a function by the breakage of a molecular bond by exposure. Further, as shown in Comparative Examples of the specification of the present application, the structural destruction or deactivation of a protein also occurs by storage after exposure to radiation. However, the structural destruction and the functional deterioration of the protein contained in the aliphatic polyester in the present invention are suppressed even when the protein is exposed to radiation, and also the structural destruction and the functional deterioration by storage after exposure are suppressed. This means that the high-order structure of the protein is retained in the composition, which is a common effect regardless of the type of the protein. It is not considered from the thickness of the aliphatic polyester through which the radiation is transmitted that this effect is due to screening, and the control mechanism is not known.

The aliphatic polyester containing the protein before radiation sterilization in the present invention may further contain an electron/ion scavenger, energy transfer agent, radical scavenger, antioxidant and plasticizer. Examples of the electron/ion scavenger include N,N'-tetramethyl phenylenediamine, diphenylenediamine, pyrene and quinone. Examples of the energy transfer agent include acenaphthene. Examples of the radical scavenger include mercaptans, octahydrophenanthrene, monoalkyl diphenyl ethers, tocopherol, citric acid, butylated hydroxyanisole, butylated hydroxytoluene, t-butyl hydroquinone, propyl gallate and ascorbic acid derivatives. Examples of the antioxidant include BHT, phosphite triesters, phenolic antiaging agents and organic thio acid salts. Additives that are generally accepted as safe for use in foods and pharmaceuticals are preferred. The amount of the additive which is not particularly limited is, for example, 0.01 to 10 wt % based on the aliphatic polyester in the sterile composition.

The aliphatic polyester containing the protein in the sterilization step preferably contains no water. The water content of the aliphatic polyester is preferably not more than 10 wt %, more preferably not more than 4 wt %, much more preferably substantially 0 wt %.

The aliphatic polyester containing the protein may be wrapped in a packaging material to be sterilized with radiation. As the packaging material, a material having high gas barrier properties such as aluminum is preferably used. The aliphatic polyester may be hermetically sealed and packaged together with a deoxidant or desiccant or while an inert gas is filled into the package after degasification, or both methods may be combined together. As the deoxidant and the desiccant, ones which do no harm to the human body and are not deactivated upon exposure to radiation are preferred.

The sterile composition of the present invention may be used as a medical material which requires the function and sterility of a protein.

EXAMPLES

The following examples are provided for the purpose of further illustrating the present invention but are in no way to be taken as limiting.

1. Measurement of Thrombin Activity

20 µL of a sample, 60 µL of a 50 mM tris-HCl (pH 8.5)+50 mM NaCl buffer and 20 µL of 0.1% PLURONIC F-68 were added to the 2008 tube of FALCON Corporation to be incubated at 37° C. for 3 minutes. Human plasma-derived purified α-thrombin (purchased from Haematologic Technologies, Inc.: HCT-0020) diluted with the above buffer to 5, 2.5, 1.25, 0.625 and 0.3125 U/mL was used as a standard. 100 µL of the S-2238 test team chromogenic substrate (1 mM: Daiichi Pure Chemicals Co., Ltd.) was added to and mixed with the obtained reaction solution under agitation to carry out a reaction at 37° C. for 5 minutes, and 800 µL of a 0.1 M citric acid solution was added to terminate the reaction. 200 µL of the reaction solution was transferred to 96 well plates to measure OD405/650.

The following method was used to measure the thrombin activity in Examples and Comparative Examples except for Examples 5 to 7 and Comparative Example 4. 20 µL of a sample and 80 µL of a diluted solution for the measurement of activity (0.01% F-68, 50 mmol/L NaCl, 50 mmol/L Tris-HCl, pH 8.4) were added to the polystyrene tube of BD to be incubated at 37° C. for 3 minutes. Recombinant thrombin (JPU Thrombin Standard 400 U/mL or WHO/US Thrombin Standard 110 IU/mL) diluted with the above buffer to 4, 2, 1, 0.5 and 0.25 U/mL in the case of JPU and to 6, 3, 1.5, 0.75 and 0.375 IU/mL in the case of IU was used as a standard. 100 µL of the S-2238 test team chromogenic substrate (1 mM: Daiichi Pure Chemicals Co., Ltd.) was added to and mixed with the obtained reaction solution under agitation to carry out a reaction at 37° C. for 7 minutes, and then 800 µL of a 0.1 M citric acid solution was added to terminate the reaction. 200 µL of the reaction solution was transferred to 96 well plates to measure OD405/650.

2. Measurement of Amount of Fibrinogen Aggregate

After the sheet was cut to a diameter of 1 cm, fibrinogen was extracted with a dilution solution to measure the amount of its aggregate by high-speed liquid chromatography.

<Test Conditions>
Detector: ultraviolet absorption photometer (measurement wavelength: 280 m)
Column: Bio Sep-SEC-s4000 (7.8×300 mm, Phenomenex)
Column temperature: 25° C.
Sampler temperature: 6° C.
Transfer phase: 0.5 mol/L Arg-HCl/50 mmol/L phosphoric acid buffer
Flow rate: 1 mL/min
Analysis time: 20 min 3. Thickness The thicknesses of 15 molded bodies were measured with a measurement force of 0.01 N by means of a high-resolution digimatic measuring unit ((LITEMATIC VL-50 of Mitutoyo Corporation) to calculate the average value as the thickness of the molded body. This measurement was carried out with minimum measurement force that could be used by the measuring unit.

4. Weight

The molded body was cut to a size of 50 mm×100 m to measure its weight so as to calculate the weight of the molded body.

5. Bulk Density

The bulk density of the molded body was calculated from the above measurement thickness and weight value.

6. Measurement of Thrombin ELISA

5 µg/mL of an antihuman thrombin antibody (No. SAHT-AP of Affinity Biologicals Inc.) was immobilized to an ELISA plate (NUNC 468667). After it was washed with PBS containing 0.05% of Tween 20, Block Ace (UK-B80 of DS Pharma Biomedical Co., Ltd.) was added to each well to carry out masking. After washing with PBS containing 0.05% of Tween 20, a test body was added. Human thrombin (HCT-0020 of Haetologic Technologies, Inc.) was used as a standard to form a calibration curve. After washing with PBS containing 0.05% of Tween 20, 0.1 µg/mL of an HRP-labelled antihuman thrombin antibody (No. SAHT- HRP of Affinity Biologicals Inc.) was added. After a reaction, the reaction product was washed with PBS containing 0.05% of Tween 20, a TMB reagent (DaKo S1599) was added, and the resulting mixture was left for 10 minutes to develop color. 1 N $H_2SO_4$ was added to stop color development so as to measure OD450-650 nm with a microplate reader.

7. Measurement of Enzyme Activities of Lipase and β-Glucosidase (1) Measurement of Extraction Rate The molded body was cut to a size of 2 cm×2 cm and immersed in 1 mL of physiological saline for 3 minutes or 3 hours to elute an immobilized enzyme. This process was carried out on three molded bodies to measure their weight changes so as to obtain the average value of extraction rate calculated from the following equation. The theoretical weight of the immobilized enzyme was calculated from the weight of the composition and wt % of the charged enzyme powder.

Extraction rate=weight loss (mg)/theoretical weight (mg) of immobilized enzyme (2) Measurement of Enzyme Activity A continuous fluorometric lipase test kit (manufactured by PROGEN BIOTECHNIK GMBH) was used to measure the activity of lipase. The recovery rate of activity was calculated from the following equation. The amount of the active enzyme was calculated in terms of concentration from the value of activity. The theoretical weight of the immobilized enzyme per unit area was calculated from wt % of the charged enzyme powder and the weight of the composition.

Recovery rate of activity (%)={amount of active enzyme ($mg/cm^2$)/theoretical weight of immobilized enzyme per unit area ($mg/cm^2$)×extraction rate)}×100

Fluorescent measurement using Tokyogreen (registered trademark, the same shall apply hereinafter)-βGlu (of Sekisui Medical Co., Ltd.) was used to measure the activity of β-glucosidase. The recovery rate of activity was calculated from the following equation. The theoretical weight of the immobilized enzyme was calculated from wt % of the charged enzyme powder and the weight of the composition.

Recovery rate of activity (%)={amount of active enzyme (mg)/theoretical weight of immobilized enzyme (mg)×extraction rate)}×100

The retention rate of activity was calculated from the following equation.

Retention rate of activity (%)={recovery rate of activity after sterilization (%)/recovery rate of activity before sterilization (%))}×100

Example 1

After thrombin-containing particles (prepared by lyophilizing an aqueous solution containing 1 mg/mL of recombinant thrombin, sodium chloride, sodium citrate, calcium chloride and mannitol and having a pH of 7) were dispersed in ethanol, dichloromethane was added to the resulting dispersion, and a polyglycolic acid-polylactic acid copolymer (Purasorb PDLG5010 of PURAC) was dissolved in the dispersion to a concentration of 10 wt % to prepare a spinning solution having a thrombin-containing particle/polyglycolic acid-polylactic acid copolymer ratio of 100 (1.69 as thrombin)/100 (w/w). Spinning was carried out by an electrospinning method to obtain a sheet-like fiber molded body. The obtained fiber molded body had a thickness of 131 μm, a weight of 1.44 $mg/cm^2$ and a bulk density of 111 $mg/cm^3$. The obtained sheet was cut to a diameter of 1 cm, and the protein was extracted with 200 μL of physiological saline to measure its activity. As a result, the measurement value of activity was 26.7 $U/cm^2$. The obtained sheet was sterilized by exposure to a 20 kGy electron beam and kept at 40° C. and 75% RH for 1 month to measure the activity of thrombin. When the activity of thrombin before sterilization was 100%, the retention rate of the activity of thrombin right after exposure to the electron beam was 79%. The retention rate of activity after 1 month was 78%, and no reduction in the activity of thrombin was observed during storage.

Example 2

After thrombin-containing particles (prepared by lyophilizing an aqueous solution containing 1 mg/mL of recombinant thrombin, sodium chloride, sodium citrate, calcium chloride and mannitol and having a pH of 7) and Quinizarin Green SS (of Tokyo Chemical Industry Co., Ltd.) were dispersed in ethanol, dichloromethane was added to the resulting dispersion, and a polyglycolic acid-polylactic acid copolymer (Purasorb PDLG5010 of PURAC) was dissolved in the dispersion to a concentration of 10 wt % to prepare a spinning solution having a thrombin-containing particle/polyglycolic acid-polylactic acid copolymer ratio of 100 (1.69 as thrombin)/100 (w/w). Spinning was carried out by the electrospinning method to obtain a sheet-like fiber molded body. The obtained sheet containing the fiber molded body (average thickness: 129 μm, weight: 1.49 $mg/cm^2$, bulk density: 124 $mg/cm^3$) was cut to a diameter of 1 cm, and the protein was extracted with 200 μL of physiological saline to measure the activity of thrombin. As a result, the measurement value of activity was 40.2 $IU/cm^2$. The obtained sheet was sterilized by exposure to a 30 kGy electron beam and kept at 40° C. and 75% RH for 1 month to measure the activity of thrombin. When the activity of thrombin before sterilization was 100%, the retention rate of the activity of thrombin right after exposure to an electron beam was 70%. The retention rate of activity after 1 month was 74%, and no reduction in the activity of thrombin was observed during storage.

Example 3

After thrombin-containing particles (prepared by lyophilizing an aqueous solution containing 1 mg/mL of recombinant thrombin, sodium chloride, sodium citrate, calcium chloride and mannitol and having a pH of 7) was dispersed in ethanol, dichloromethane was added to the resulting dispersion, and a polyglycolic acid-polylactic acid copolymer (Purasorb PDLG5010 of PURAC) was dissolved in the dispersion to a concentration of 10 wt % to prepare a dope solution having a thrombin-containing particle/polyglycolic acid-polylactic acid copolymer ratio of 100 (1.69 as thrombin)/100 (w/w). The obtained dope solution was used to form a film by a casting method. The coating interval was 127 μm, and the coating speed was 30.1 mm/sec. The obtained sheet had a thickness of 58 μm, a weight of 2.9 $mg/cm^2$ and a bulk density of 504 $mg/cm^3$. The obtained sheet was cut to a diameter of 1 cm, and the protein was extracted with 200 μL of physiological saline to measure the activity of thrombin. As a result, the measurement value of activity was 71.1 $IU/cm^2$. The obtained sheet was sterilized by exposure to a 30 kGy electron beam and kept at 40° C. and 75% RH for 1 month to measure the activity of thrombin. When the activity of thrombin before sterilization was 100%, the retention rate of the activity of thrombin right after exposure to an electron beam was 75.7%. The retention rate of activity after 1 month was 82%, and no reduction in the activity of thrombin was observed during storage.

Example 4

After fibrinogen-containing particles (prepared by lyophilizing an aqueous solution containing 10 mg/mL of recombinant fibrinogen, arginine, sodium chloride and mannitol and having a pH of 8.5) were dispersed in ethanol, dichloromethane was added to the resulting dispersion, and a polyglycolic acid-polylactic acid copolymer (Purasorb PDLG5010 of PURAC) was dissolved in the dispersion to a concentration of 10 wt % to prepare a spinning solution having a fibrinogen-containing particle/polyglycolic acid-polylactic acid copolymer ratio of 100 (50.85 as fibrinogen)/100 (w/w). Spinning was carried out by the electrospinning method to obtain a sheet-like fiber molded body. The obtained fiber molded body had a thickness of 131 μm, a weight of 1.44 mg/cm$^2$ and a bulk density of 110 mg/cm$^3$. The obtained sheet was cut to a diameter of 1 cm, and fibrinogen was extracted with a dilution solution to measure the amount of its aggregate by high-speed chromatography. As a result, the amount of the aggregate was 9.79%. The obtained sheet was sterilized by exposure to a 30 kGy electron beam and kept at 40° C. and 75% RH for 1 month to measure the amount of the aggregate. The amount of the aggregate right after exposure to an electron beam was 18.81%. The weight of the aggregate after 1 month was 24.14%.

Comparative Example 1

After a 30 kGy electron beam was applied to thrombin-containing particles (prepared by lyophilizing an aqueous solution containing 1 mg/mL of recombinant thrombin, sodium chloride, sodium citrate, calcium chloride and mannitol and having a pH of 7) to sterilize them, the thrombin-containing particles were kept at 40° C. and 75% RH for 1 month to measure the activity of thrombin. The activity of thrombin before exposure was 404.73 U/vial. When the activity of thrombin before sterilization was 100%, the retention rate of the activity of thrombin right after exposure to an electron beam was 51.8%. The retention rate of activity after 1 month was 17.9%, and a reduction in the activity of thrombin was observed during storage.

Comparative Example 2

After thrombin-containing particles (prepared by lyophilizing an aqueous solution containing 1 mg/mL of recombinant thrombin, sodium chloride, sodium citrate, calcium chloride and mannitol and having a pH of 7) were dispersed in 2-propanol, hydroxypropyl cellulose (2.0-2.9 mPa·s, manufactured by Nippon Soda Co., Ltd.) was dissolved in the resulting dispersion to a concentration of 13 wt % to prepare a dope solution having a thrombin-containing particle/hydroxypropyl cellulose ratio of 100/100 (w/w). Spinning was carried out by the electrospinning method to obtain a sheet-like fiber molded body. The obtained fiber molded body had a thickness of 204 μm, a weight of 2.08 mg/cm$^2$ and a bulk density of 101 mg/cm$^3$. The obtained sheet was cut to a diameter of 1 cm, and the protein was extracted with 200 μL of physiological saline to measure its activity. As a result, the measurement value of activity was 110.3 IU/cm$^2$. The obtained sheet was sterilized by exposure to a 30 kGy electron beam and kept at 40° C. and 75% RH for 1 month to measure the activity of thrombin. When the activity of thrombin before sterilization was 100%, the retention rate of the activity of thrombin right after exposure to an electron beam was 68.4%. The retention rate of activity after 1 month was 54.9% and a reduction in the activity of thrombin was observed during storage.

Comparative Example 3

After a 30 kGy electron beam was applied to fibrinogen-containing particles (prepared by lyophilizing an aqueous solution containing 10 mg/mL of recombinant fibrinogen, arginine, sodium chloride and mannitol and having a pH of 8.5) to sterilize them, the thrombin-containing particles were kept at 40° C. and 75% RH for 1 month to measure the amount of an fibrinogen aggregate. The amount of the aggregate before exposure was 6.97%. The amount of the aggregate right after exposure to an electron beam was 18.51%. The amount of the aggregate after 1 month was 54.72%.

Figure 1:
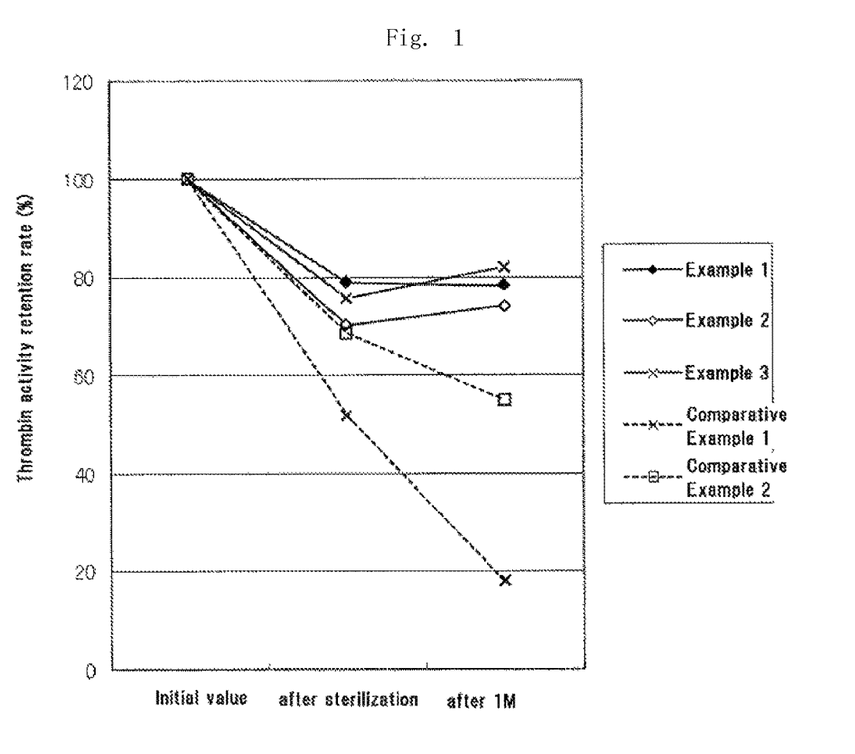
FIG. 1 shows each of thrombin activities obtained by measuring the thrombin-containing sheet-like fiber molded bodies of the present invention obtained in Examples 1 and 2, the thrombin-containing film of the present invention obtained in Example 3, the thrombin-containing particle of Comparative Example 1 and the comparative thrombin-containing sheet-like fiber molded body obtained in Comparative Example 2 as the retention rates (%) of a value after sterilization and a value after 1 month of storage after sterilization based on an initial value before sterilization.

The results (the retention rates of activity of thrombin (Th) after sterilization and after storage after sterilization based on the value before sterilization) of Examples 1 to 3 and Comparative Examples 1 and 2 are shown in FIG. 1.

It is understood that when the protein is contained in the aliphatic polyester, the structural change and functional deterioration of the protein caused by radiation sterilization are suppressed as compared with a case where only protein-containing particles are used (Comparative Example 1) and further that the change and the deterioration caused by storage after radiation sterilization are suppressed as compared with a case where not the aliphatic polyester but a cellulose (hydroxypropyl cellulose) is used (Comparative Example 2).

Figure 2:
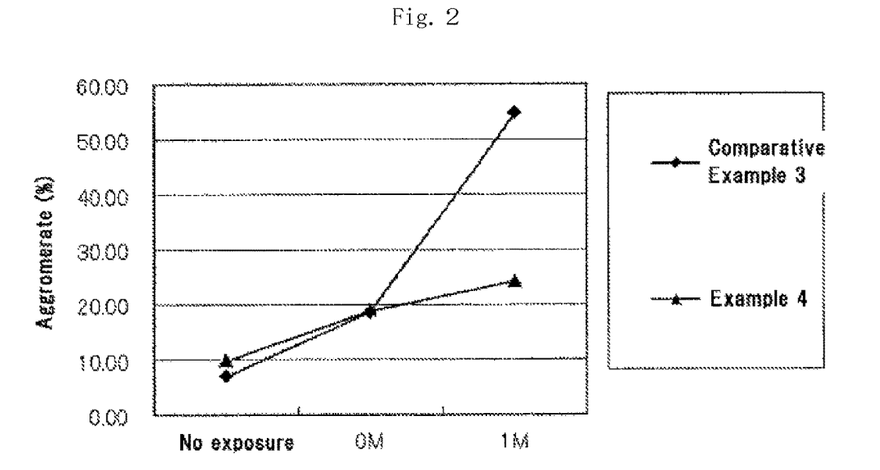
FIG. 2 shows the amounts of fibrinogen aggregates obtained by measuring the fibrinogen-containing sheet-like fiber molded body of the present invention obtained in Example 4 and the fibrinogen-containing particle of Comparative Example 3 when they are not irradiated, after they are sterilized (OM) and after 1 month of storage after sterilization (1M).

The results (the amount of the fibrinogen aggregate after sterilization and after storage after sterilization) of Example 4 and Comparative Example 3 are shown in FIG. 2.

It is understood that when the protein is contained in the aliphatic polyester (Example 4), the structural change of the protein caused by storage after radiation sterilization is suppressed as compared with a case where only protein-containing particles are used (Comparative Example 3).

Example 5

After thrombin-containing particles (Bolheal, (registered trademark, the same shall apply hereinafter), tissue adhesive: Vial 3) were dispersed in ethanol, dichloromethane was added to the resulting dispersion, and polylactic acid (PL18 of Purac Biomaterials) was dissolved in the dispersion to a concentration of 10 wt % to prepare a spinning solution having a thrombin-containing particle/polylactic acid ratio of 40 (0.45 as thrombin)/100 (w/w). Spinning was carried out by the electrospinning method to obtain a sheet-like fiber molded body. The obtained sheet was sterilized with a 20 kGy electron beam. The obtained sheet was cut to a size of 2 cm×2 cm, and the protein was extracted with 1 mL of physiological saline to measure its activity and ELISA. As a result, the activity measurement value was 5.0 U/cm$^2$, and the ELISA measurement value was 3.4 μg/cm$^2$. When activity and ELISA measurements were made on an unsterilized sheet likewise, the activity measurement value was 7.5 U/cm$^2$ and the ELISA measurement value was 4.35 μg/cm$^2$.

That is, the retention rate of the activity of the sterilized sheet was 73% of that of the unsterilized sheet.

Example 6

After thrombin-containing particles (Bolheal tissue adhesive: Vial 3) were dispersed in ethanol, dichloromethane was added to the resulting dispersion, and polylactic acid (PL18 of Purac Biomaterials) was dissolved in the dispersion to a concentration of 10 wt % to prepare a spinning solution having a thrombin-containing particle/polylactic acid ratio of 70 (0.78 as thrombin)/100 (w/w). Spinning was carried out by the electrospinning method to obtain a sheet-like fiber molded body. The obtained sheet was sterilized with a 20 kGy electron beam. The obtained sheet was cut to a size of 2 cm×2 cm, and the protein was extracted with 1 mL of physiological saline to measure its activity and ELISA. As a result, the activity measurement value was 9.575 U/cm$^2$, and the ELISA measurement value was 7.0 μg/cm$^2$. When activity and ELISA measurements were made on an unsterilized sheet likewise, the activity measurement value was 11.15 U/cm$^2$ and the ELISA measurement value was 7.2 μg/cm$^2$. That is, the retention rate of the activity of the sterilized sheet was 86% of that of the unsterilized sheet.

Example 7

After thrombin lyophilized powders (Bolheal tissue adhesive: Vial 3) were dispersed in ethanol, dichloromethane was added to the resulting dispersion, and polylactic acid (PL18 of Purac Biomaterials) was dissolved in the dispersion to a concentration of 10 wt % to prepare a spinning solution having a thrombin lyophilized powder/polylactic acid ratio of 100 (1.1 as thrombin)/100 (w/w). Spinning was carried out by the electrospinning method at a temperature of 22° C. and a humidity of not more than 26% to obtain a sheet-like fiber molded body. The inner diameter of a jet nozzle was 0.8 mm, the voltage was 15 kV, the flow rate of the spinning solution was 3.0 mL/h, and the distance from the jet nozzle to a flat plate was 25 cm. The obtained sheet was sterilized with a 20 kGy electron beam. The obtained sheet was cut to a size of 2 cm×2 cm, and the protein was extracted with 1 mL of physiological saline to measure its activity and ELISA. As a result, the activity measurement value was 15 U/cm$^2$, and the ELISA measurement value was 11 μg/cm$^2$. When activity and ELISA measurements were made on an unsterilized sheet likewise, the activity measurement value was 23 U/cm$^2$ and the ELISA measurement value was 16 μg/cm$^2$. That is, the retention rate of the activity of the sterilized sheet was 64% of that of the unsterilized sheet.

Comparative Example 4

Thrombin-containing particles (Bolheal) were sterilized with a 20 kGy electron beam. The protein was extracted with 1 mL of physiological saline to measure its activity and ELISA. As a result, the activity measurement value was 22.5 U/cm$^2$ and the ELISA measurement value was 11.5 μg/cm$^2$. When activity and ELISA measurements were made on unsterilized thrombin-containing particles likewise, the activity measurement value was 68.5 U/cm$^2$ and the ELISA measurement value was 41.5 μg/cm$^2$. That is, the retention rate of the activity of the sterilized sheet was 32% of that of the unsterilized sheet.

Example 8

After lipase powders (derived from pig pancreas, manufactured by Wako Pure Chemical Industries, Ltd., the same shall apply hereinafter) were dispersed in ethanol, dichloromethane was added to the resulting dispersion, and a polylactic acid-glycolic acid copolymer (PDLG5010 of Purac Biomaterials) was dissolved in the dispersion to a concentration of 10 wt % to prepare a spinning solution having a lipase powder/polylactic acid-glycolic acid copolymer ratio of 50/100 (w/w). Spinning was carried out by the electrospinning method at a temperature of 27° C. and a humidity of not more than 25% to obtain a sheet-like fiber molded body. The inner diameter of a jet nozzle was 0.9 mm, the voltage was 15 kV, the flow rate of the spinning solution was 4.0 mL/h, and the distance from the jet nozzle to a flat plate was 25 cm. The lipase extraction rate of the obtained sheet was 79%. The obtained sheet was sterilized with a 20 kGy electron beam. The obtained sterilized sheet was cut to a size of 1 cm×1 cm, and lipase was extracted with 1 mL of a lipase buffer contained in a kit to measure its activity. As a result, the recovery rate of activity was 100%.

Example 9

Dichloromethane was added to lipase powders, and a polylactic acid-glycolic acid copolymer (PDLG5010 of Purac Biomaterials) was dissolved in the resulting mixture to a concentration of 10 wt % to prepare a spinning solution having a lipase powder/polylactic acid ratio of 50/100 (w/w). Spinning was carried out by the electrospinning method at a temperature of 26° C. and a humidity of not more than 25% to obtain a sheet-like fiber molded body. The inner diameter of a jet nozzle was 0.8 mm, the voltage was 15 kV, the flow rate of the spinning solution was 4.0 mL/h, and the distance from the jet nozzle to a flat plate was 25 cm. The lipase extraction rate of the obtained sheet was 63%. The obtained sheet was sterilized with a 20 kGy electron beam. The obtained sterilized sheet was cut to a size of 1 cm×1 cm, and lipase was extracted with 1 mL of a lipase buffer contained in a kit to measure its activity. As a result, the recovery rate of activity was 92%.

Example 10

After β-glucosidase powders (derived from almond, manufactured by Oriental Yeast Co., Ltd, the same shall apply hereinafter) were dispersed in ethanol, dichloromethane was added to the resulting dispersion, and a polylactic acid-glycolic acid copolymer (PDLG5010 of Purac Biomaterials) was dissolved in the dispersion to a concentration of 10 wt % to prepare a spinning solution having a β-glucosidase powder/polylactic acid-glycolic acid copolymer ratio of 38/62 (w/w). Spinning was carried out by the electrospinning method at a temperature of 27° C. and a humidity of not more than 25% to obtain a sheet-like fiber molded body. The inner diameter of a jet nozzle was 0.9 mm, the voltage was 15 kV, the flow rate of the spinning solution was 4.0 mL/h, and the distance from the jet nozzle to a flat plate was 25 cm. After the obtained sheet was cut to a size of 2 cm×2 cm, it was sterilized with a 20 kGy electron beam. β-glucosidase was extracted with 1 mL of physiological saline to measure its activity with Tokyogreen-βGlu. As a result, the recovery rate of activity was 92%. When activity measurement was made on an unsterilized sheet likewise, the recovery rate of activity was 94%. It was understood from above that the retention rate of the activity of the sterilized fiber molded body was 98% of that of the unsterilized fiber molded body and that β-glucosidase was not deactivated by electron beam sterilization.

Example 11

After β-glucosidase powders were dispersed in ethanol, dichloromethane was added to the resulting dispersion, and a polylactic acid-caprolactone copolymer (PLCA8812 of Taki Chemical Co., Ltd.) was dissolved in the dispersion to a concentration of 10 wt % to prepare a spinning solution having a β-glucosidase powder/polylactic acid-caprolactone copolymer ratio of 38/62 (w/w). Spinning was carried out by the electrospinning method at a temperature of 27° C. and a humidity of not more than 25% to obtain a sheet-like fiber molded body. The inner diameter of a jet nozzle was 0.9 mm, the voltage was 15 kV, the flow rate of the spinning solution was 3.0 mL/h, and the distance from the jet nozzle to a flat plate was 25 cm. After the obtained sheet was cut to a size of 2 cm×2 cm, it was sterilized with a 20 kGy electron beam. β-glucosidase was extracted with 1 mL of physiological saline to measure its activity with Tokyogreen-βGlu. As a result, the recovery rate of activity was 81%. When activity measurement was made on an unsterilized sheet likewise, the recovery rate of activity was 80%. It was understood from above that the retention rate of the activity of the sterilized fiber molded body was 101% of that of the unsterilized fiber molded body and that β-glucosidase was not deactivated by electron beam sterilization.

Example 12

After β-glucosidase powders were dispersed in ethanol, dichloromethane was added to the resulting dispersion, and polylactic acid (PL18 of Purac Biomaterials) was dissolved in the dispersion to a concentration of 11 wt % to prepare a spinning solution having a β-glucosidase powder/polylactic acid ratio of 38/62 (w/w). Spinning was carried out by the electrospinning method at a temperature of 27° C. and a humidity of not more than 25% to obtain a sheet-like fiber molded body. The inner diameter of a jet nozzle was 0.9 mm, the voltage was 15 kV, the flow rate of the spinning solution was 3.0 mL/h, and the distance from the jet nozzle to a flat plate was 25 cm. After the obtained sheet was cut to a size of 2 cm×2 cm, it was sterilized with a 20 kGy electron beam. β-glucosidase was extracted with 1 mL of physiological saline to measure its activity with Tokyogreen-βGlu. As a result, the recovery rate of activity was 62%. When activity measurement was made on an unsterilized sheet likewise, the recovery rate of activity was 71%. It was understood from above that the retention rate of the activity of the sterilized fiber molded body was 87% of that of the unsterilized fiber molded body and that β-glucosidase was not deactivated by electron beam sterilization.

Comparative Example 5

Lipase powders were sterilized with a 20 kGy electron beam. 1 mL of a lipase buffer was added to 1 mg of the powders to measure the activity of lipase. As a result, the recovery rate of activity was 74%.

Comparative Example 6

β-glucosidase powders were sterilized with a 20 kGy electron beam. 2 mg of the powders was dissolved in 1 mL of physiological saline to measure the activity of β-glucosidase with Tokyogreen-βGlu. As a result, the retention rate of activity was 81%.

EFFECT OF THE INVENTION

The sterile composition of the present invention retains the structure and function of a protein though it is sterilized.

INDUSTRIAL FEASIBILITY

The sterile composition of the present invention is used in the manufacturing industry of medical products which require the function and sterility of a protein.

The invention claimed is:

1. A sterile composition sterilized with radiation comprising an aliphatic polyester and a protein selected from the group consisting of fibrinogen, enzymes, transport proteins, defense proteins, toxin proteins, protein hormones, growth factors and mixtures thereof, wherein at least part of the protein enters the inside of the aliphatic polyester as dispersion of particles of the protein or particles of a mixture of the protein and pharmaceutically acceptable additives, and wherein the sizes of the particles are not less than 0.01 μm.

2. The sterile composition according to claim 1, wherein the aliphatic polyester is selected from the group consisting of polyglycolic acid, polylactic acid, polycaprolactone, copolymers thereof and mixtures thereof.

3. The sterile composition according to claim 1 which is in a fiber form.

4. The sterile composition according to claim 3 which is produced by an electro spinning method.

5. The sterile composition according to claim 1 which is in a film form.

6. The sterile composition according to claim 5 which is produced by a casting method.

* * * * *